United States Patent [19]

Archer et al.

[11] Patent Number: 5,710,305

[45] Date of Patent: Jan. 20, 1998

[54] FLAME RETARDANT PRODUCT AND PROCESS

[75] Inventors: Adrian Charles Archer, West Midlands; Christopher John Harris, Worcester; Gary Woodward, Kidderminster; Mohsen Zakikhani, Harborne, all of England

[73] Assignee: Albright & Wilson UK Limited, West Midlands, England

[21] Appl. No.: 691,119

[22] Filed: Aug. 1, 1996

[30] Foreign Application Priority Data

Aug. 16, 1995 [GB] United Kingdom ............... 9516794

[51] Int. Cl.$^6$ .................................................. C07F 9/6574
[52] U.S. Cl. ............................ 558/77; 558/83; 524/117
[58] Field of Search ........................ 558/77, 83; 524/117

[56] References Cited

U.S. PATENT DOCUMENTS 3,789,091  1/1974  Anderson et al. ................. 558/77
3,849,368  11/1974 Anderson et al. ................. 524/117

Primary Examiner—Michael G. Ambrose
Attorney, Agent, or Firm—Frishauf, Holtz, Goodman, Langer & Chick, P.C.

[57] ABSTRACT

A method for producing alkyl derivatives of phosphonic acids together with hexyl-bis[5-ethyl-2-hexyl-1,3,2-dioxaphosphorinan-5-yl)methyl]ester, P,P'dioxide as a novel product and the use of such a product as, or in connection with, a flame retardant.

21 Claims, No Drawings

FLAME RETARDANT PRODUCT AND PROCESS

The present invention provides a method of the synthesis of flame retardants, in particular flame retardants of the general formula (I):

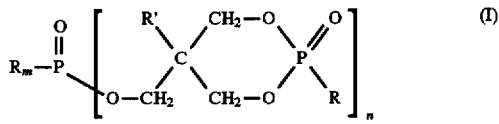

wherein each R is independently a linear, branched or cyclic alkyl or alkenyl group or ester or alkoxylate thereof, and R' is a linear, branched or cyclic alkyl or alkenyl group, m is 0, 1 or 2, n is 1, 2 or 3 and (n+m) is 3. Alternatively the R' group may be an alkaryl, aryl, aralkyl, haloaryl, aryloxyalkyl, haloaryloxyalkyl, or hydroxyalkyl group.

The present invention also provides a novel phosphonic acid, hexyl-, bis[(5-ethyl-2-hexyl-1,3,2-dioxaphosphorinan-5-yl)methyl]ester, P,P' dioxide. The present invention further provides a flame retardant having the aforesaid formula (I), its use as or in connection with flame retardants, and materials made flame retardant thereby.

Flame retardants are incorporated into many products on the grounds of safety in order to control the spread of fire through the product. Flame retardants can, for example, act by causing rapid extinguishing of flames, or by making the product difficult to set alight. Whilst flame retardants have conventionally been used to treat fabrics, soft furnishings etc. and have been incorporated inter alia into paints and resins such as epoxy resins, many other applications are now being actively pursued, especially within the electronic, automotive, aerospace and construction industries.

Examples of flame retardants of the general formula (I) are given in U.S. Pat. No. 3,789,091 (corresponding to GB 1418497) and U.S. Pat. No. 3,849,368 where the methyl to octyl analogues are described. However, the only analogues described where both the R groups may be of the same alkyl chain length, are the methyl to butyl analogues.

Conventionally, and as described in Example 1a of U.S. Pat. No. 3,789,091, said methyl analogue of general formula (I) is produced by way of the reaction at approximately 200° C. between a bicyclic phosphite and dimethyl methyl phosphite (DMMP). In the industrial preparation of said methyl analogue a catalyst, e.g. an Arbusov (alkyl halide) is typically used. However, the reaction has several disadvantages, eg. the reaction is not commercially viable for the industrial preparation of flame retardants of general formula (I) which comprise R groups other than methyl. Also, the reaction requires more extreme conditions for the preparation of the ethyl and the butyl analogue. Thus the conventional method does not provide an efficient and useful method for the production of many of the analogues of general formula (I).

Because of the increasing use of, and demand for, flame retardants there is a need to provide a more economical method of the industrial synthesis of the known flame retardants of general formula (I). Moreover, in order to fulfil the varying requirements of the many different applications in which flame retardants have conventionally, and are now beginning to be used, there is a need to provide a wider range of compounds of said general formula than has hitherto been available. For example flame retardants in different physical forms, and of varying viscosities may be required, dependent upon the application.

We have now discovered that the reaction of a bicyclic phosphite with phosphorous acid, phosphoric acid, hypophosphorous acid or any derivative or suitable salt thereof to produce a phosphite of general formula (III), followed by reaction of said phosphite with an alkene having at least one α-unsaturated bond, in the presence of a free radical initiator provides a more economical route to the manufacture of flame retardants of general formula (I), than was hitherto available. Furthermore, the present method provides a purer product that has previously been available which is believed to be due to a reduction in the polymerisation of the bicyclic phosphite (II). We have further discovered that the aforementioned reaction provides compounds of general formula (I) wherein the R group is $C_5$ or higher, which were previously unobtainable by the conventional industrial synthesis method. The viscosity of the flame retardants of the present invention appears to be inversely proportional to the length of the R group.

Thus, the present invention provides a method for the production of more mobile flame retardants of the general formula (I), than has hitherto been obtainable. Such mobile flame retardants are of particular advantage in for use in polyurethanes where liquid flame retardants are preferred.

Accordingly, in a first embodiment, the present invention provides a method of producing a flame retardant of general formula (I):

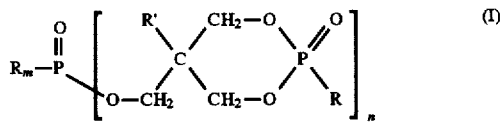

wherein each R is independently a linear, branched or cyclic alkyl or alkenyl group or an ester or alkoxylate thereof, preferably a $C_2$ to $C_{22}$ linear, branched or cyclic alkyl or alkenyl chain, and R' is a linear, branched or cyclic alkyl or alkenyl chain, preferably a $C_1$ to $C_6$ linear, branched or cyclic alkyl or alkenyl chain; m is 0, 1 or 2, n is 1, 2 or 3 and (n+m) is 3. Alternatively the R' group may be an alkaryl, aryl, aralkyl, haloaryl, aryloxyalkyl, haloaryloxyalkyl, or hydroxyalkyl group.

said method comprising as a first step:

(a) reacting a bicyclic phosphite of general formula (II):

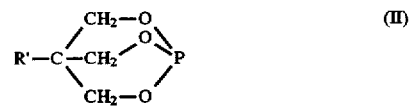

wherein R' is as hereinabove defined, with phosphorous acid, phosphoric acid, hypophosphorous acid, phosphonic acid or any suitable derivative or salt thereof, in a molar ratio sufficient to produce a phosphite of general formula (III):

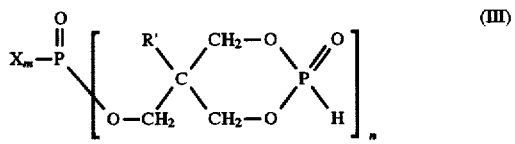

wherein R', n and m are hereinabove defined, and each X is independently an H, OH, an alkyl or alkenyl group or ester or alkoxylate thereof preferably a $C_2$ to $C_{22}$ alkyl or alkenyl group, or mixture thereof and as a second step:

(b) reacting said phosphite (III) with a linear, branched or cyclic alkene or alkyne or substituted alkene or alkyne which has at least one α-unsaturated bond, preferably a $C_2$ to $C_{22}$ linear, branched or cyclic alkene in the presence of a free radical initiator to produce said flame retardant.

3 and optionally as a third step:

(c) purifying said flame retardant.

In a second embodiment, the present invention provides a novel flame retardant of general formula (I), wherein R is a hexyl group, said flame retardant being phosphonic acid, hexyl-bis[(5-ethyl-2-hexyl-1,3,2-dioxaphosphorinan-5-yl) methyl]ester, P,P' dioxide.

In a third embodiment, the present invention provides the use of flame retardants of general formula (I) as, or in connection with flame retardants, and materials made flame retardant thereby.

According to a particularly preferred embodiment of the present invention, the present invention provides a method of producing a flame retardant of general formula (I), according to the method of the first embodiment, wherein said R group is individually a $C_2$ to $C_{12}$ alkyl group or ester thereof, and said R' group is a $C_2$ group.

The bicyclic phosphite (II) may be prepared in situ prior to the reaction method herein described to produce the phosphite (III), eg. by the known reaction of trimethylolpropane and trimethylphosphite in the presence of methyl acid pyrophosphate to produce said bicyclic phosphite. Alternatively the isolate bicyclic phosphite may be used as the starting material.

Phosphorous acid, phosphoric acid, hypophosphorous, phosphonic acid or any suitable derivative or salt thereof may be used to produce the phosphite (III). Suitable derivatives include alkyl phosphonic acids, dialkyl phosphinic acids, and monoalkyl alkyl phosphonates. The alkyl phosphonic acid may for example be a $C_1$ to $C_{22}$ alkyl phosphonic acid, preferably a $C_2$ to $C_{10}$ alkyl phosphonic acid, eg. octyl phosphonic acid. The dialkyl phosphonic acid may be, for example, a $C_1$ to $C_{22}$ dialkyl phosphonic acid, wherein the two alkyl groups may be the same or different, eg. dipropyl phosphinic acid. The monoalkyl alkyl phosphonate may for example be monobutyl phosphonate. The acids may be added either as a solid, for example octyl phosphonic acid, or as a liquid, for example phosphoric acid or molten phosphorous acid. Suitable salts may include, for example, phosphates.

The molar ratio of the bicyclic phosphite to the number of free acid groups of said acid is typically within the range 1.2:1 to 1:1.5, preferably 1.1:1 to 1:1.4, most preferably 1:1 to 1:1.3. It is especially preferred that the ratio is 1:1, ie. such that appreciable amounts of the bicyclic phosphite do not remain unreacted in the reaction mixture. However, a slight stiochiometric excess of the acid may be tolerated, dependent upon the purification methods used.

The reaction of the bicyclic phosphite with said acid (step a) is typically carried out under reflux at a temperature of 90° C. to 180° C. for 0.5 to 10 hours, preferably 100° C. to 160° C. for 1 to 3 hours. However, the exact temperature and reaction time will depend upon the reactants employed, and the conditions used. Furthermore, longer reaction times may be required if the reaction mixture is kept below its reflux temperature.

The alkene may be a straight, branched or cyclic chain alkene, or alkyne or substituted alkene or alkyne preferably a $C_2$ to $C_{22}$ alkene, most preferably a $C_2$ to $C_{16}$ alkene eg. a $C_2$ to $C_{10}$ alkene. Any such alkene with a α-unsaturated bond may be used. Suitable examples of the linear chain alkene include ethylene, 1-butene, 1-hexene and 1-octene. Examples of the branched and cyclic chain alkenes include 2-methyl-2-hexene and methylene cyclohexene. Alternatively, alkenes with a α-unsaturated bond and one or more further unsaturated bonds eg. dienes and trienes such as 1,5 hexadiene and 1,3,5 hexatriene may be used. Alter-

4 natively a mixed alkene system, for example 1-hexene and 1-octene may be used. Suitable alkynes include acetylene and methyl acetylene, propargyl alcohol, butyne-1,4-diol, acetylene carboxylic acid esters, phenyl acetylene and dialkyl acetylenes.

If the alkene is a liquid, eg. 1-hexene, it may be added by simple addition to the reaction mixture, or if the alkene is a gas, eg 1-butene, it may be bubbled through said reaction mixture under increased atmospheric pressure.

The molar ratio of phosphite (III) to alkene is dependent upon the number of free acid groups of the phosphite (III). Typically it is within the range of 1:0.7 to 1:5 preferably 1:0.8 to 1:4 most preferably 1:1 to 1:3. It is especially preferred that the ratio is such that no substantial amount of unreacted phosphite remains in the reaction mixture.

Any conventional free radical initiator may be used according to the present invention. Suitable examples include amongst others, alkyl peroxides, eg tertiary butyl peroxide, hydroperoxides, hydrogen peroxide and azobisisobutyronitrile. Typically, the free radical initiator will be present in amounts of up to 10 mole %, preferably up to 5 mole %, most preferably up to 3 mole %, eg. 2 mole % based on the amount of said alkene. The free radical initiator may be added to the reaction mixture either as a single additional or in aliquots either before, during or after the addition of the alkene. Alternatively, the free radicals may be generated by the use of UV radiation, ionising radiation, ultrasound or any other non-chemical means, or the addition reaction could be carried out under suitable base catalysis conditions.

The reaction of the phosphite (III) with the alkene (step b) is typically carried out over 1 to 50 hours at a temperature of 100° C. to 200° C. dependent upon the reaction conditions and the reagents employed, for example 10 to 35 hours at 130° C. to 160°. The reaction is maintained for such time as is necessary to produce the flame retardant of general formula (I).

The purification of the reaction mixture to isolate the product may be by any conventional purification technique. A particularly preferred method of purification by is the addition of an alkyl halide, for example butyl bromide, to the reaction mixture. According to a particular purification technique the butyl bromide is added to the reaction mixture, either as the total amount or in aliquots, in a total amount of up to 5 mole % based on the amount of bicyclic phosphite. Typically amounts of up to 2 mole % of the butyl bromide are used. The reaction mixture is then maintained at a temperature of a 100° C. to 200° C., eg 160° C. to 190° C., for 1 to 15 hours, eg 3 to 10 hours.

The purified reaction product of general formula (I) may be isolated from the reaction mixture by any suitable isolation technique, for example removal by vacuum stripping of said mixture.

The flame retardants of the present invention may be used in any conventional application. Particular use of the flame retardants may be made as additives to polyurethanes, epoxy resins and composites, phenolics, paints, varnishes and textiles. Examples of the use of said flame retardants includes use in printed circuit boards and soft furnishings, for example in the automotive, aerospace and construction industries.

The present invention will be further illustrated by reference to the following examples.

EXAMPLE 1

The Synthesis of the Hexyl Analogue of General Formula (I)

The ethyl bicyclic phosphite (II) (324 g, 2 moles) in a reflux apparatus at 100° C., molten phosphorous acid (82 g, 1 mole) was added in portions over 20 minutes. The reaction mixture was then heated to 120° C. and maintained at this temperature for 1 hour, to produce the phosphite (III). The reaction mixture was then heated to 140° C. A mixture of 1-hexene (252 g, 3 moles) and tertiary-butyl peroxide (5 g, 1 mole %) was added dropwise to the reaction mixture over a period of 12 hours to produce the hexyl analogue of general formula (I).

To remove any remaining traces of the bicyclic phosphite, butyl bromide (4 g, 1 mole %) was slowly added to the reaction mixture, which was then heated to 180° C. and maintained at this temperature for 6 hours. After this time the reaction mixture was vacuum stripped for 1 hour (180° C., 30 mm Hg) to isolate said hexyl analogue.

The product was a viscous yellow liquid, produced in a yield of 650 g (98.8% theoretical yield). Analysis of the reaction product by Fast Atom Bombardment Mass Spectroscopy (FAB M-S) showed a peak at 659 represent a molecular mass of 658+H$^+$. The molecular formula of the reaction product is $C_{30}H_{61}O_9P_3$, and the molecular mass is 658. Therefore the FAB M-S provided positive identification of the reaction product as phosphonic acid, hexyl-, bis[(5-ethyl-2-hexyl-1,3,2-dioxaphosphrinan-5-yl)methyl]ester, P,P′ dioxide.

EXAMPLE 2

The Synthesis of the Butyl Analogue of General Formula (I)

The phosphite (III) was prepared according to the method given in Example 1. 1-Butene gas was bubbled with stirring through the phosphite reaction mixture for 35 hours with the reaction mixture maintained at approximately 140° C. Portions of tertiary-butyl-peroxide (10 g, 2 mole %) were added to the stirred reaction mixture. After the 35 hours butyl bromide (4 g, 1 mole %) was added to the reaction mixture which was heated to 160° C. and maintained at this temperature for a further 6 hours until the reaction product of general formula (I) was obtained. The reaction mixture was vacuum stripped (180° C., 30 mm Hg) for 1 hour to isolate the product.

The product was a viscous, yellow liquid produced in a yield of 540 g (approximately 94.1% theoretical yield). It is believed the molecular formula of the reaction product $C_{24}H_{49}O_9P_3$, and the molecular weight is 574.

EXAMPLE 3

The Synthesis of the Octyl Analogue of General Formula (I)

The bicyclic phosphite (II) (121.5 g, 0.75 moles) was prepared as according to Example 1. The reaction mixture was stirred and maintained at 100° C. whilst octyl phosphonic acid (73 g, 0.375 moles) was added over 30 minutes. The reaction mixture was then heated to 160° C. and maintained at this temperature for 10 hours until the phosphite (III) was produced. The mixture was cooled to 150° C. and 1-octene (84 g, 0.75 moles) and tertiary butyl peroxide (2 g, 2 mole %) were added in aliquots to the reaction mixture over 10 hours. Butyl bromide (1 g, 1 mole %) was then added to the reaction mixture, which was then heated to 180° C. and maintained at this temperature for 6 hours until the reaction product of general formula (I) was obtained. The reaction mixture was vacuum stripped (180° C., 30 mm Hg) for 1 hour to isolate the product.

The product was a viscous yellow liquid produced in a yield of 270 g (97% of theoretical yield). It is believed the molecular formula of the reaction product is $C_{10}H_{73}O_9P_3$ and the molecular mass is 742.

EXAMPLE 4

The Synthesis of an Oligomeric 1,2-Ethanediyl/hexyl Analogue

The phosphite (III) (406 g; 1 mole) was prepared according to the method given in Example 1.

Acetylene gas was bubbled with stirring through the phosphite reaction mixture for 10 hours, with the reaction mixture maintained at 140° C. Portions of tertiary-butyl peroxide (5 g; 1 mole %) were added to the reaction mixture during this time. A mixture of 1-hexene (202 g; 2.4 moles) and tertiary-butyl peroxide (5 g; 1 mole %) was added dropwise to the reaction mixture over the following period of 12 hours to produce an oligomeric 1,2-ethanediyl/hexyl analogue of general formula (I), with the reaction temperature maintained at 140° C.

Butyl bromide (4 g; 1 mole %) was added to the reaction mixture, which was heated to 180° C. and maintained at this temperature for a further 6 hours. The reaction mixture was vacuum stripped (140° C.; 5 mm Hg) for 1 hour to isolate the product.

The product was a viscous, pale yellow liquid produced in a yield of 590 g.

EXAMPLE 5

The Synthesis of a Monocyclic Butyl Analogue

The bicyclic phosphite (II) (243 g; 1.5 moles) was prepared as according to Example 1. The reaction mixture was stirred and maintained at 100° C. whilst monobutyl butyl phosphonate (291 g; 1.5 moles) was added over 45 minutes. The reaction mixture was heated at 160° C. for 3 hours, then 180° C. for 3 hours, then 190° C. for 6 hours and 200° C. for a further 6 hours, to produce a phosphite (III) (1.5 moles) of formula:

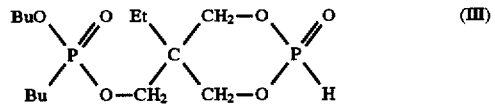

1-Butene gas was bubbled with stirring into the reaction mixture for 10 hours, with the reaction mixture maintained at 140° C. Portions of tertiary-butyl peroxide (5 g; 2 mole %) were added to the reaction mixture during this time.

Following the gas addition, butyl bromide (3 g; 1 mole %) was added to the reaction mixture which was then heated at 180° C. for 6 hours. The mixture was then vacuum stripped for 2 hours (20 mm Hg; 180° C.). The product was a mobile liquid, produced in a yield of 575 g (93.0% of theoretical yield).

Analysis of the reaction product by Fast Atom Bombardment Mass Spectroscopy (FAB-MS) showed a peak at 413 representing a molecular mass of 412+H$^+$. The molecular formula of the reaction product is $C_{18}H_{38}O_6P_9$, and the molecular mass is 412. This provided positive identification of the reaction product as phosphonic acid, butyl-, (5-ethyl-2-butyl-1,3,2-dioxaphosphorinane-5-yl)methyl, butyl ester, P-oxide, i.e.:

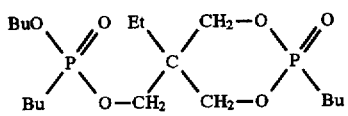

(I)

EXAMPLE 6

Determination of the Flame Retardant Capacity of Example 1 and Example 3

The flame retardants of Example 1 and Example 3 were tested as flame retardants for epoxy resins. The two examples were tested in a standard Bisphenol A based high temperature cure formulation (see below), according to the UL94 vertical burning test procedure using a sample thickness of both 1.6 mm and 3.2 mm (see below).

(i) The following Bisphenol A based epoxy resin high temperature cure formulation was prepared:

| Example | Weight | |
|---|---|---|
| | 4A | 4B |
| *Bisphenol A-epichlorohydrin epoxy resin (number average molecular weight ≦ 700) | 51.2 g | 51.2 g |
| Dicyandiamide | 3.2 g | 3.2 g |
| 2-methylimidazole | 0.3 g | 0.3 g |
| Hexyl analogue (21.3% of total weight) | 14.8 g | — |
| Octyl analogue (24.0% of total weight) | — | 17.3 g |
| | 59.5 g | 72.0 g |

*1 - available commercially as Epikote 828 from Shell. Epikote is a trademark.

The hexyl and octyl analogues were mixed into formulations A and B respectively in the given amount so as to produce a resin with a target phosphorus content of 3% by weight. Said analogues contain 14.1% phosphorus and 12.5% phosphorus respectively. The formulations were mixed thoroughly and degassed under vacuum at 80° C. The formulations were cured overnight at 150° C. in PTFE moulds measuring 127 mm×12.7 mm×1.6 mm or 3.2 mm.

(ii) Flame Retardancy Test Results

The flame retardancy performance of Examples 4A and 4B are given below in Table 1.

TABLE 1

Flame retardancy of Examples 4A and 4B

| SAMPLE | UL94 RATING | |
|---|---|---|
| | 1.6 mm THICKNESS | 3.2 mm THICKNESS |
| Sample 4A | V0 | V0 |
| Sample 4B | V1 | V0 |

Both examples 4A and 4B produced a significant improvement in the flame retardancy of the epoxy resins. Furthermore the cure times of the epoxy resin formulation was acceptable. The minimum amount of the hexyl and octyl analogues flame retardants of general formula (I) as used in Example 4A and 4B required to produce a V0 rating may be less than the actual amount shown.

We claim:

1. A method of producing a flame retardant of general formula (I):

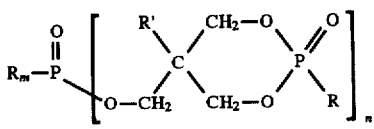

(I)

in which R is independently selected from the group consisting of linear, branched or cyclic alkyl, alkenyl, and provided that R bonded to the cyclic phosphorus atom is not alkoxy, alkoxyl, R' is selected from the group consisting of linear, branched or cyclic alkyl, alkenyl, alkaryl, aryl, aralkyl, haloaryl, aryloxyalkyl, haloaryloxyalkyl, and hydroxyalkyl, m is 0, 1 or 2, n is 1, 2 or 3 and (n+m) is 3 wherein said method comprises a first step and a second step, and optionally a third step, said first step comprising:

(a) reacting a bicyclic phosphite of general formula (II):

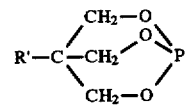

(II)

wherein said R' is as hereinabove defined, with an acid selected from the group consisting of phosphorous acid, phosphoric acid, hypophosphorous acid, phosphonic acid and derivatives or salts thereof, in a molar ratio sufficient to produce a phosphite of general formula (III):

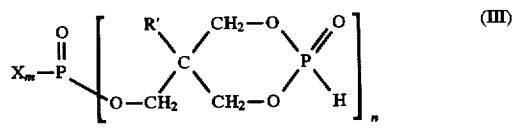

(III)

wherein said R', n and m are as hereinabove defined, and each X is independently selected from the group consisting of H, OH, alkyl, alkenyl, and alkoxy, and mixtures thereof and said second step comprising:

(b) reacting said phosphite (III) with an alkene or alkyne selected from the group consisting of linear, branched or cyclic alkenes or alkynes, and substituted alkenes or alkynes which have at least one α-unsaturated bond, in the presence of a free radical initiator to produce said flame retardant of general formula (I)

and said optional third step comprising:

(c) purifying said flame retardant.

2. The method of claim 1, in which each said R group is independently selected from the group consisting of $C_2$ to $C_{22}$ alkyl, alkenyl, and alkoxy.

3. The method of claim 1, in which said R' group is selected from the group consisting of $C_1$ to $C_6$ alkyl, alkenyl, and alkoxy.

4. The method of claim 1, in which each said R group is independently selected from the group consisting of $C_2$ to $C_{12}$ alkyls and said R' is $C_2$ alkyl.

5. The method of claim 1, in which said acid is selected from the group consisting of $C_1$ to $C_{22}$ alkyl phosphonic acids and dialkyl phosphinic acids.

6. The method of claim 1 in which said acid is a monoalkyl alkyl phosphonate.

7. The method of claim 6 in which said monoalkyl alkyl phosphonate is monobutyl butyl phosphonate.

8. The method of claim 1, in which said molar ratio of the bicyclic phosphite (II) to the number of free acid groups of said acid is within the range of 1.2:1 to 1:1.5.

9. The method of claim 1, in which the reaction of said bicyclic phosphite (II) and said acid is carried out at 90° C. to 180° C. for 0.5 to 10 hours.

10. The method of claim 1, in which said alkene is selected from the group consisting of $C_2$ to $C_{22}$ alkenes.

11. The method of claim 10, in which said $C_2$ to $C_{22}$ alkene has one or more further unsaturated bonds.

12. The method of claim 1, in which the molar ratio of said phosphite (III) to said alkene or alkyne or substituted alkene or alkyne is within the range 1:0.7 to 1:5.

13. The method of claim 1, in which said alkyne is acetylene.

14. The method of claim 1, in which said free radical initiator is selected from the group consisting of peroxides and azobisisobutylnitriles.

15. The method of claim 14, in which said free radical initiator is present in an amount of up to 10 mole %, based on the amount of said alkene, or alkyne or substituted alkene or alkyne.

16. The method of claim 1, in which said free radical initiator consists of a non-chemical source selected from UV radiation, ionising radiation and ultra sound radiation.

17. The method of claim 1, wherein the reaction of said phosphite (III) with said alkene or alkyne or substituted alkene or alkyne is carried out over 1 to 50 hours at 100°–200° C.

18. The method of claim 1, wherein said optional third step (c) consists essentially of purifying said flame retardant (I) by means of adding an alkyl halide.

19. The method of claim 18, wherein said alkyl halide is present in an amount of up to 5 mole % based on the amount of said bicyclic phosphite (II).

20. The method of claim 18, in which said alkyl halide is a butyl bromide.

21. The method of claim 18, in which said flame retardant (I) is purified at a temperature of 100° C. to 200° C. for 1 to 15 hours.

* * * * *